(12) United States Patent
Daito et al.

(10) Patent No.: US 8,141,619 B2
(45) Date of Patent: Mar. 27, 2012

(54) FIN INSPECTION METHOD OF A HEAT EXCHANGER

(75) Inventors: Akihiro Daito, Handa (JP); Kaoru Okazoe, Anjo (JP); Atsushi Fukumoto, Nishio (JP); Tomoaki Yoshimori, Okazaki (JP); Saburou Nagaino, Okazaki (JP)

(73) Assignee: Denso Corporation, Kariya (JP)

( * ) Notice: Subject to any disclaimer, the term of this patent is extended or adjusted under 35 U.S.C. 154(b) by 419 days.

(21) Appl. No.: 12/461,249

(22) Filed: Aug. 5, 2009

(65) Prior Publication Data

US 2010/0044004 A1 Feb. 25, 2010

(30) Foreign Application Priority Data

Aug. 21, 2008 (JP) .................................. 2008-213113
Jul. 30, 2009 (JP) .................................. 2009-178009

(51) Int. Cl.
*B60H 1/00* (2006.01)
(52) U.S. Cl. ...................................... 165/11.1; 382/141
(58) Field of Classification Search .................. 165/11.1, 165/11.2; 382/141, 152; 702/81, 82
See application file for complete search history.

(56) References Cited

U.S. PATENT DOCUMENTS

| | | | |
|---|---|---|---|
| 2010/0027871 A1* | 2/2010 | Daito et al. | 382/141 |
| 2010/0027872 A1* | 2/2010 | Daito et al. | 382/141 |

FOREIGN PATENT DOCUMENTS

| | | | |
|---|---|---|---|
| JP | 2002250611 A | * | 9/2002 |
| JP | A-2002-250611 | | 9/2002 |
| JP | A-2005-292066 | | 10/2005 |
| JP | 2005321300 A | * | 11/2005 |
| JP | A-2005-321300 | | 11/2005 |
| JP | A-2006-208372 | | 8/2006 |

OTHER PUBLICATIONS

Japanese Office Action in Japanese Patent Application No. 2009-178009; dated Nov. 2, 2010 (with English-language translation).

* cited by examiner

*Primary Examiner* — Judy Swann
*Assistant Examiner* — Devon Russell
(74) *Attorney, Agent, or Firm* — Oliff & Berridge, PLC

(57) ABSTRACT

A fin inspection method comprising a step of having an imaging device capture an image of the core and inputting into an image processing device the image data for storage, a step of setting a first region in the image data in which an image of the entire core is captured and setting a second region in which an image of at least a portion of all of the tubes is captured so as to identify position information of the tubes, a step of setting a third region for fin detection between adjacent tubes based on the identified position information of the tubes, a step of performing binarization and noise removal in the third region to obtain an image of the fins and identifying from the image of the fins the edge position information of the fins along a long direction of the tubes, and a step of performing statistical processing of the pitch intervals based on the edge position information of the fins and judging fin defects.

5 Claims, 13 Drawing Sheets

FREQUENCY OF
CUMULATIVE SUM
WAVEFORM OF FINS

FIN POSITION

FIN INSPECTION METHOD OF A HEAT EXCHANGER

BACKGROUND OF THE INVENTION

1. Field of the Invention

The present invention relates to a fin inspection method of a heat exchanger, more particularly relates to a fin inspection method of a fin-and-tube type heat exchanger used in automotive heaters and the like.

2. Description of the Related Art

FIG. 1 is a perspective view showing a fin-and-tube type heat exchanger 10 generally used in automotive heaters and the like. FIG. 2 is an enlarged view of the fin and tube parts wherein the heat exchanger 10 of FIG. 1 is rotated 90 degrees. The heat exchanger 10 is provided with a core 11 serving as a heat exchanger part. The core 11 is provided with a plurality of tubes 12 through which a fluid serving as a heat exchange medium passes and a large number of fins 13 that are attached to the surfaces of the tubes to increase the heat transfer area. Reference numerals 14 indicate tank parts, 15 side plates, and 16 sheet metal.

The core 11 of the fin-and-tube type heat exchanger 10 is formed by a plurality of unit elements, each provided with one straight tube 12 and a fin 13 attached in a bellows-like state on its surface, regularly repeated and connected. In such a unit element, the fin 13 is comprised of a flat sheet folded into an S-shape which is repeated to form a bellows shape. The fin 13 is therefore a folded part provided with a plurality of curved parts. Defects in the tubes 12 and fins 13 of such a heat exchanger can be detected by appearance inspection with a considerable success rate. Such appearance inspection has been improved for automation, labor-saving, and raising accuracy up to now. Recently, inspection methods making use of image processing have been introduced.

As such an inspection method using image processing, the inspection method such as shown in Japanese Unexamined Patent Publication (A) No. 2005-321300 is known.

This inspection method is an appearance inspection method of a core of a heat exchanger having a repeated pattern of the two components of a tube and fin. According to this inspection method, two images are captured in order to apply a fault detection method using image processing. One of the images of the part being inspected is an image captured as a tube inspection image while controlling the illumination so that the brightness of the image of the fin part is suppressed. The other inspection image is captured as a fin inspection image by an illumination by which the fin part can be inspected.

Further, a two-dimensional Fourier transform is applied to these tube or fin inspection images to obtain inspection images at the spatial frequency domains. Next, for example, parts of the input images are utilized to prepare mask image data for samples of good parts and this data is used to remove the frequency components of the good parts from the inspection images. Then, a two-dimensional inverse Fourier transform is further applied to obtain fault detection images.

However, when using the aforementioned prior art for inspecting fins, the following problems have occurred. That is, in order to extract a fin, it was necessary to capture two inspection images at illuminations suitable for the tubes or the fins. Since the images are captured while adjusting the level of the brightness, differences in the surface conditions of a workpiece have become a cause of detection errors in inspection.

In fin inspection, transformed images of the inspection images obtained by application of a fast Fourier transform (FFT) and the transformed images of a normal fin part of the inspection image are used to find defects, so unless all of the fins of a normal fin part are at equal pitches, good precision detection of defective fins is not possible. Further, by applying an FFT to the entire core, factors leading to detection errors will occur and the amount of data will end up becoming massive. In the case of FFT analysis, the transforms have to be applied twice, for regular and inverse, or else defects cannot be detected, thus causing the processing speed to drop. When performing inspection processing using FFT analysis, judgment based on the dimensional threshold value was difficult.

As buckled fins, to be explained later, occur at equal pitches, there is the possibility that buckled fins may not be detected with good precision by the previous methods.

FIG. 3 shows examples of fin defects.

As modes of defects of the fins, as shown in FIG. 3, there are short fins, crushing, buckling, irregular pitch, erosion, residual flux, etc. The concepts of these fin defects are shown below, but these are not necessarily strict definitions.

When a distance between an end of the fins along the tube direction and sheet metal 16 is within certain constant range, the fins are classified as normal in length, while when otherwise, they are classified as fin defects called "short fins".

Short fins occur in the case of fins having an abnormal length in the tube direction, for example, in the case where the fins are not bent at the prescribed intervals in the tube axis direction or in the case where fins of different specifications are mistakenly attached.

If there are for example 20 rows of fins, there will be side plates and packing at the first and 20th rows, thus the fin lengths along the tube direction will not be normal at the first and 20th rows of fins. Rows at which short fins have occurred, excluding the first and 20th rows, from the second to 19th rows are classified as having short fin defects. The first and 20th rows are referred to as the "outermost rows", while the second to 19th rows excluding the outermost rows are referred to as rows other than the "outermost rows".

"Crushing" is the bending of the upper and lower ends (the upper and lower ends in the vertical direction when the core surface shown in FIG. 2 is placed horizontally) of a fin that occurs when a fin is pressed from above by some sort of force. When the amount of crushing is large, the flow of air between the fins is hindered.

"Buckling" is a defect occurring at the end parts of the stack of fins (in the previous example, the first and 20th outermost rows). This refers to cases where a side plate is struck by something etc. causing the side plate to deform and along with this, the fins also ending up deforming.

"Irregular pitch" is an irregularity which occurs when the normal allowable range of the pitch of a fin is exceeded. Here, it is defined as what remains when other categorized defect modes (crushing etc.) are excluded.

"Erosion" is a defect in which a fin has melted from the heat in a furnace. The pitch of the fin ends up becoming larger at that portion.

"Residual flux" is the deposition of foreign matter such flux residue on a fin.

Up until now, these defects could not be automatically identified.

SUMMARY OF THE INVENTION

To solve the aforementioned problems, the aspect of the invention of claim 1 is an inspection method of a core of a heat exchanger provided with fins and tubes comprising a step of having an imaging device capture an image of the core and inputting into an image processing device the image data for storage, a step of setting a first region in the image data in which an image of the entire core is captured and setting a second region in which an image of at least a portion of all of the tubes is captured so as to identify position information of the tubes, a step of setting a third region for fin detection between adjacent tubes based on the identified position information of the tubes, a step of performing binarization and noise removal in the third region to obtain an image of the fins and identifying from the image of the fins the edge position information of the fins along a long direction of the tubes, and a step of performing statistical processing of the pitch intervals based on the edge position information of the fins and judging fin defects.

Due to this, it is possible to perform inspection of fins with a high accuracy and possible to increase the processing speed.

The aspect of the invention of claim 2 is an inspection method of a core of a heat exchanger as set forth in claim 1 further comprising a step of performing processing on the image of the fins at the third region, for adding brightness of the image in a direction perpendicular to the long direction of the tube, across the long direction of the tube to obtain a waveform across the long direction of the tube and a step of analyzing the waveform by wavelet analysis to find a total sum of frequency components added together in a predetermined frequency range across the long direction of the tube to judge fin defects.

Due to this, in fin defect inspection, it is possible to further increase the fin defect judgment accuracy by frequency analysis and possible to avoid ending up judging something which should be deemed a defect as a good part.

The aspect of the invention of claim 3 is an inspection method of a core of a heat exchanger as set forth in claim 1 further comprising a step of setting a fourth region for short fin detection encompassing the upper end or lower end of all of the tubes and a step of calculating the distance between a tank part of a core of the heat exchanger and the fin edge position in the greatest proximity with it in a common region of the third region and the fourth region to judge fin defects.

Due to this, similar to the aspect of the invention of claim 1, it is possible to inspect with high accuracy and possible to inspect for short fin defects.

The aspect of the invention of claim 4 is an inspection method of a core of a heat exchanger as set forth in claim 1 further comprising a step of extracting an entire single tube from the image data, then finding the smallest rectangle surrounding the tube and calculating the width of the tube to judge fin defects.

Due to this, similar to the aspect of the invention of claim 1, it is possible to inspect with high accuracy and possible to calculate the widths of the tubes so as to further improve the accuracy of inspection for buckling defects and the like of the fins.

The aspect of the invention of claim 5 is an inspection method of a core of a heat exchanger as set forth in claim 1, wherein the third region for fin detection between adjacent tubes is corrected according to an average of angles of inclination of the tubes. Due to this, fin parameters are detected with better accuracy.

BRIEF DESCRIPTION OF THE DRAWINGS

These and other objects and features of the present invention will become clearer from the following description of the preferred embodiments given with reference to the attached drawings, wherein:

FIG. 1 is a perspective view showing a fin-and-tube type heat exchanger 10 generally used in an automotive heater and the like;

DESCRIPTION OF THE PREFERRED EMBODIMENTS

Figure 4:
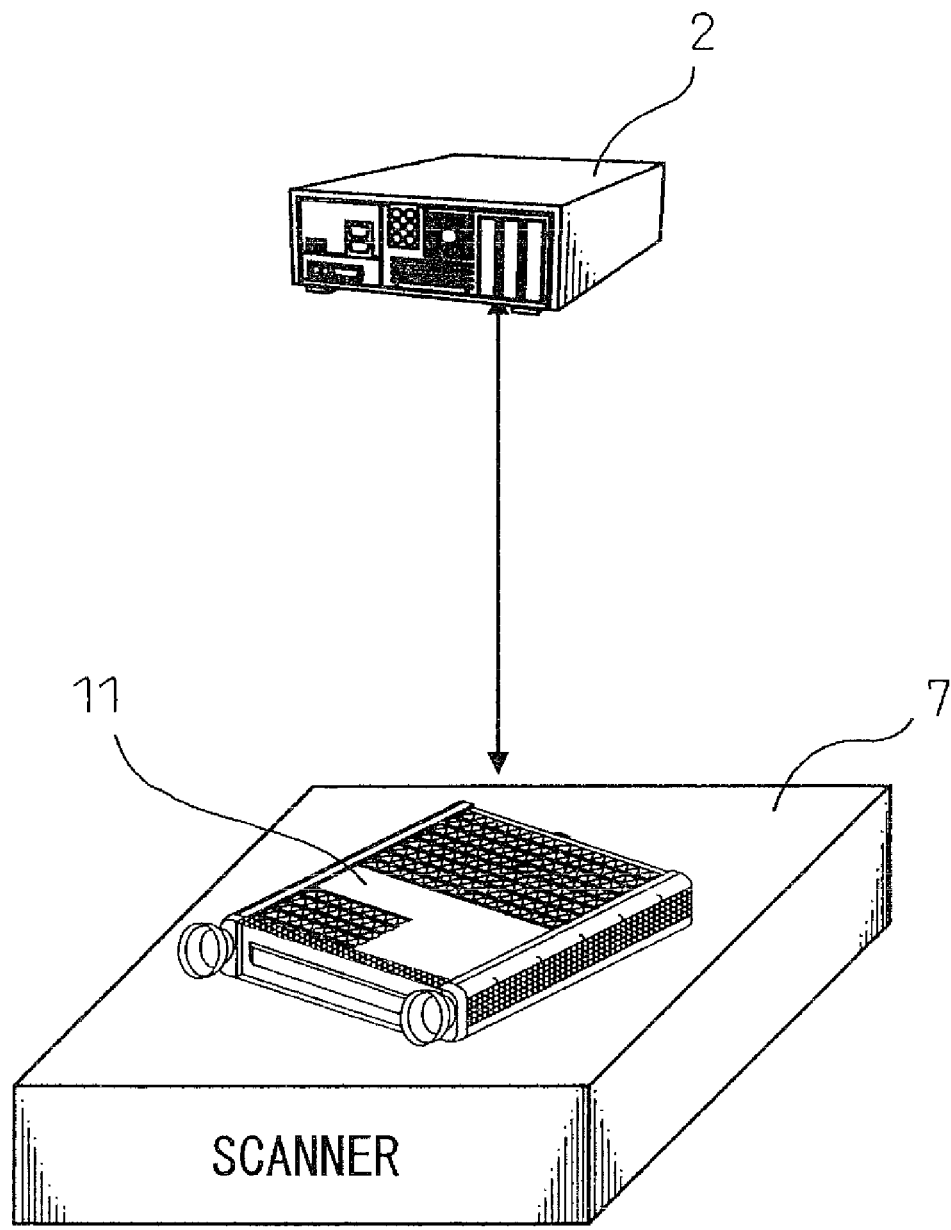
FIG. 4 is a schematic view of a system using the fin inspection method using a scanner.
Figure 5:
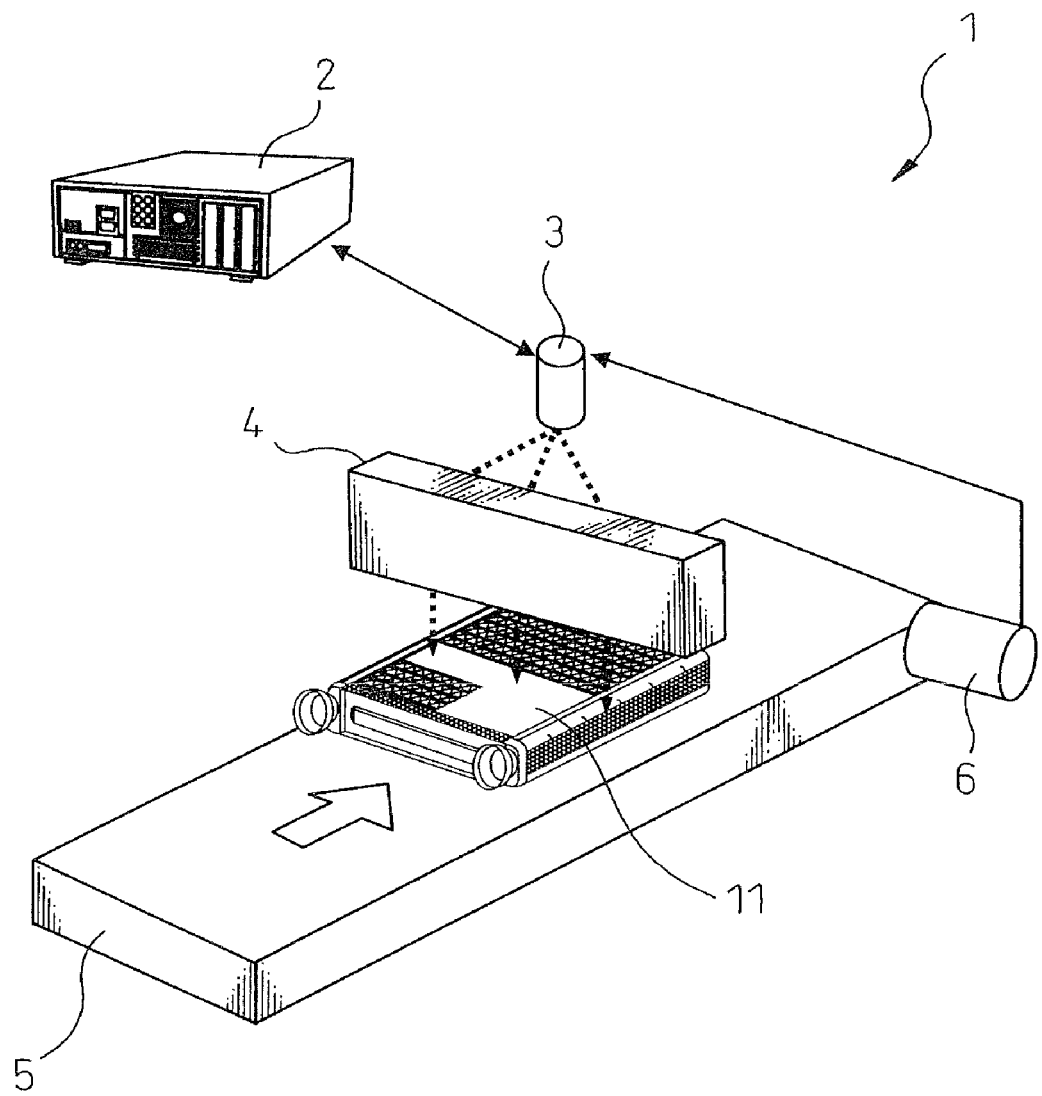
FIG. 5 is a schematic view of a system using the fin inspection method using a belt conveyor.

FIG. 4 is a schematic view of a system using a fin inspection method using a scanner. FIG. 5 is a schematic view of a system using a fin inspection method using a belt conveyor.

Below, referring to FIG. 5, an embodiment of the present invention concerning a fin inspection method in the case of using a belt conveyor will be explained.

In the following embodiment, the object of inspection is a core 11 of a fin-and-tube type heat exchanger 10 used in automotive heaters and the like. Each component element of the fin-and-tube type heat exchanger being inspected is designated by the same reference notation as in FIG. 1.

The system 1 shows an inspection system for inspecting a top surface of the core of the fin-and-tube type heat exchanger 10. In the inspection of the bottom surface of the core as well, an inspection system 1 having a similar configuration is used to perform inspection using a similar operation. The system 1 of the fin inspection method is provided with an image processing device 2, a CCD camera or other imaging device 3, a focusing (lens)/illumination device 4, a belt conveyor 5, and an encoder 6 (not necessarily required) coupled to a drive unit of the belt conveyor.

In response to a signal from the encoder 6, the illumination device 4 illuminates the core 11 of the heat exchanger being inspected. The imaging device 3 captures an image of the tubes and the fins of the core part and sends image data to the image processing device 2. The image processing device 2 converts this from an analog to digital format, then converts the image to 256 tone image data and stores it as raw image data in a storage means.

In a fin inspection method in the case of using a scanner 7 as shown in FIG. 4, the following processing is similar to that of the fin inspection method in the case of using a belt conveyor of FIG. 5.

As seen in FIG. 4, when the scanner 7 and core 11 are placed curved, the angle of the image data is appropriately corrected by the image processing device.

To set the range of processing for the raw image data, first a reference position is determined and a first window is set with respect to the raw image data. In the first window, the reference position is determined while setting the long direction of the tube as the Y-axis.

As the method of determining the reference position, as one example, it is possible to set the reference position by having the core 11 conveyed on a belt conveyor along a conveyor guide, having the image capturing means 3 detect the tip of the core 11, and comparing this against already input product dimension data obtained from the product number information. When positioning the core 11 at the scanner 7 when capturing images, the reference position may be calculated from the production dimension data. Also, it is possible to set the reference position by processing the image and finding the overall external shape.

An example of setting the windows for fin inspection when setting the reference position at the center of the core 11 will be explained below.

Figure 1:
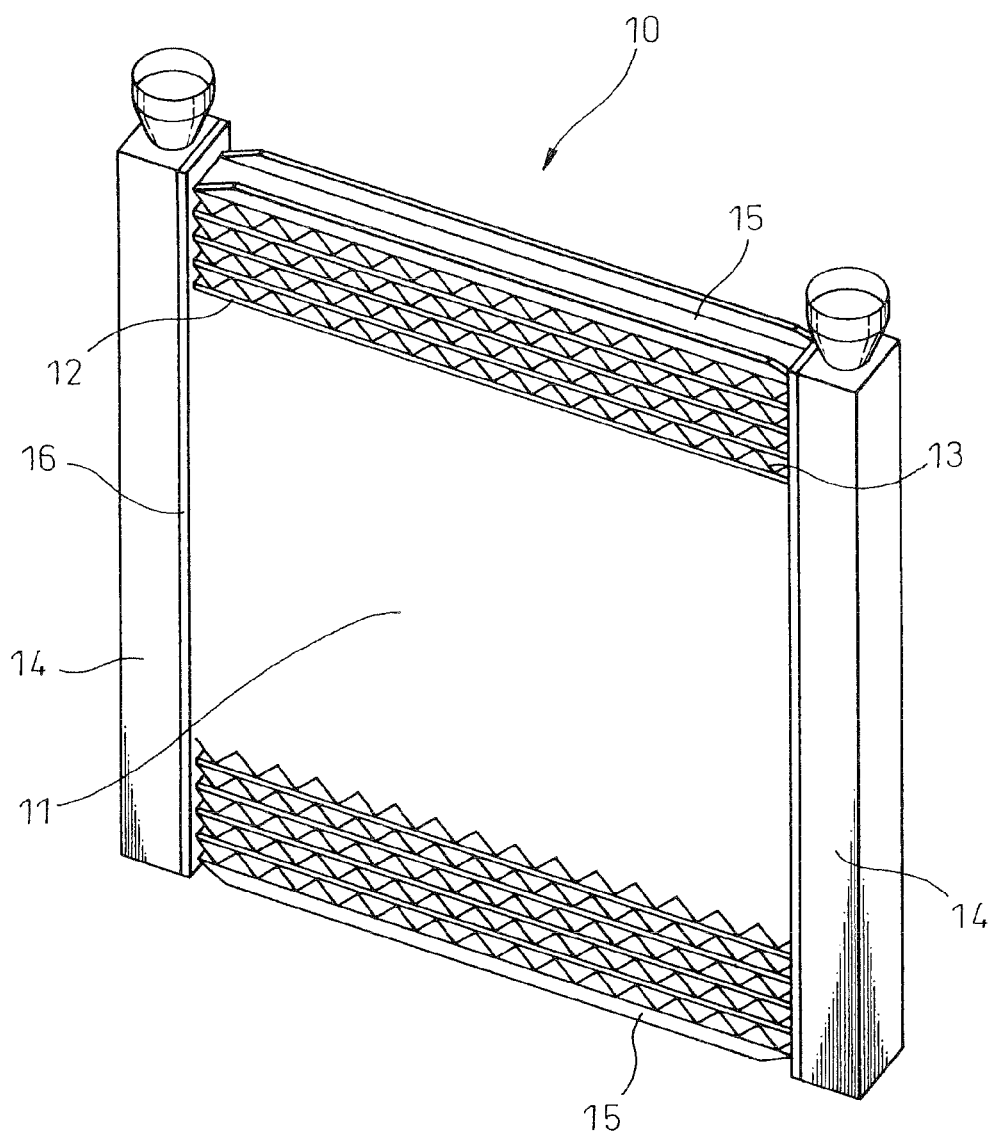
Figure 6:
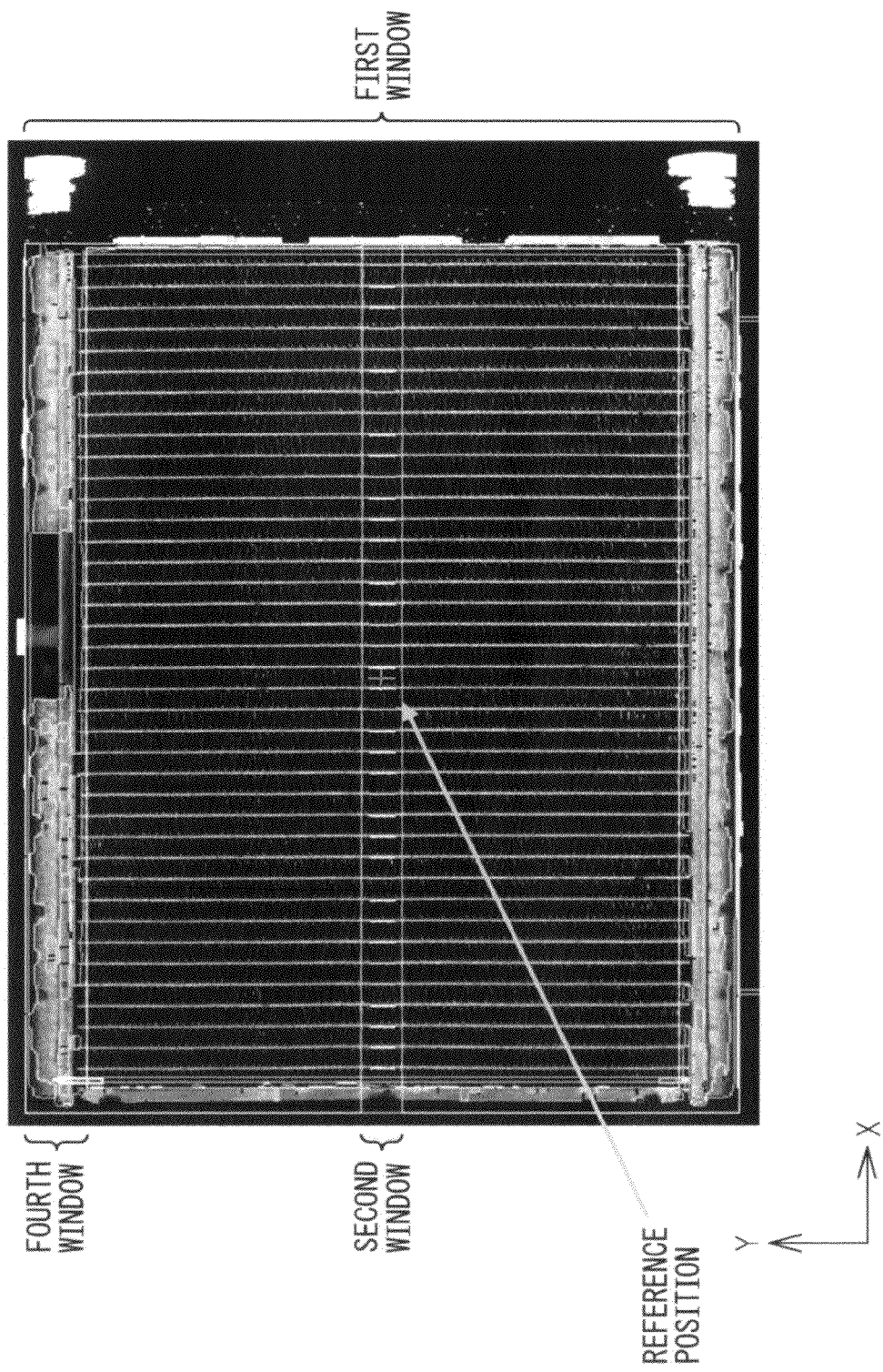
FIG. 6 is a view for explaining the setting of windows for fin inspection.

FIG. 6 is a view for explaining the setting of windows for fin inspection. The photograph of FIG. 6 is somewhat unclear, however, the cross at the center represents the reference position. The white frame long in the X-axis direction at the center is the second window. The white frames long in the X-axis direction at the top or the bottom are the fourth windows. The series of white lines along the Y-axis direction represent the tubes. FIG. 6 is a state in which the core 11 of the perspective view of FIG. 1 is rotated by 90 degrees. In FIG. 6, tanks 14 and sheet metal 16 are located at the top and bottom ends of the paper surface along the Y-axis direction and side plates 15 are located at the left and right ends.

When setting of the windows in the explanation below, the X-Y coordinates are set with the long direction of all of the tubes as the Y-axis.

First, the second window for detecting the tubes will be explained. This window is a window necessary for setting the fin detection third window to be explained later. The second window, as shown in FIG. 6, is a rectangular window long in the X-axis direction (horizontal width L1 and vertical length L2) and having the reference position as its center. The second window is designated by converting the value from the reference position (that is, the size of ½ of L1, L2) to pixel units and inputting the result.

Next, to find the edges of the two sides of the X-axis direction of each tube in the second window, a known edge detection processing is performed, and the coordinates of the X-axis direction of the edges of the two sides of each tube (left edge and right edge) are stored.

As another method, the second window W is divided into small regions and, for each small region, averaging is performed on the raw image data. In this case, the fins remain and the tube disappears. The thus obtained image is referred to as an "averaged image". For example, if the tube width is 10 pixels, a small region having 30 pixels in an X-axis direction and 1 pixel in a Y-axis direction may be explained. The image processing means obtains the difference between the brightness of the averaged image and the brightness of the raw image. As a result, an image of only the tube can be extracted from the raw image. If an image of only the tube is extracted, the X-coordinates of the white and black boundary of the tube may be made the edges of the two sides of each tube.

In this way, the edge coordinates are calculated from the edges of the two sides of each tube in the second window. Further, the pitch between the tubes, the number of tubes, and the tube width may also be calculated.

Next, the fourth window will be explained. This window is a window necessary for detecting short fins to be explained later. A fourth window is a rectangular window long in the X-axis direction (horizontal width L1 and vertical length L3). Fourth windows are set at the top and the bottom where the tank parts 14 and sheet metal 16 are present as shown in FIG. 6 by designating the distance from the reference position from the product number information of pixel units. The positional coordinates of the sheet metal 16 are already known from the product number information.

Figure 7:
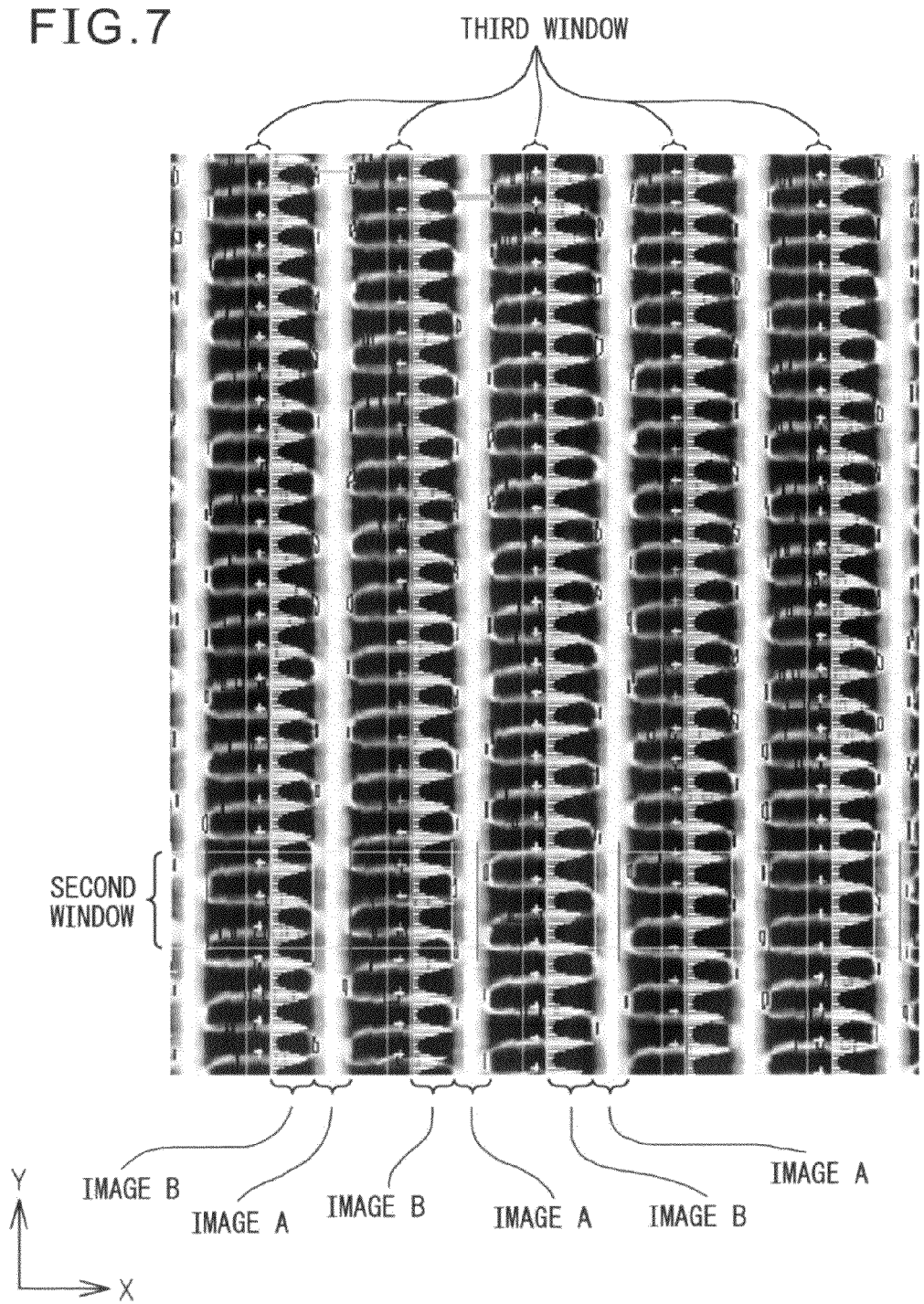
FIG. 7 is a view in which images B for frequency analysis of the fins are superimposed over partial enlarged views of FIG. 6.

FIG. 7 is a view in which images B for frequency analysis of the fins are superimposed over partial enlarged views of FIG. 6. Images A show the tubes.

Third windows long in the Y-axis direction are prepared based on the edge coordinates of the two sides of each tube in the second window. The third windows are fin inspection windows and are respectively set between adjacent tubes, including the tank parts 14 at the top and bottom ends of the tubes. Third windows are set between all adjacent tubes.

In manufacturing the core of the heat exchanger, a parallelogram-shape core is sometimes formed. This parallelogram-shape core is not a defect in the case where slopes of parallel sides in the long direction of the tubes are within an allowance range close to 90 degrees. When the images of the tubes are extracted in the above method, the angles of inclination of the tubes can be calculated. Third windows may be corrected so as to be inclined along the long direction of the tubes, according an average of the angles of inclination of the tubes. Due to this, fin parameters are detected with better accuracy.

When the third windows are set, image processing is performed to detect the fins inside each individual third window. Binarization is performed and images of the fins are extracted with a threshold value. Noise removal processing is performed on the fin images. At this time, after closing processing is performed to remove noise at the regions where the third windows overlap with the fourth windows, a threshold value different from the above threshold value is preferably used to detect the Y-axis direction gaps between the tips of the fins and the sheet metal 16.

Using the above images of fins to be extracted, the following processing is performed next to judge for fin defects. Based on the obtained fin images, the fin edges seen from the Y-axis direction are extracted at the third windows. In FIG. 7, the crosses (upper edge) in the third windows are extracted as borders turning from black to white. The positions of the edges turning from white to black (the lower edges which are lower by exactly the width of the fins) and the number of these crosses are also found. Based on the position coordinates of the upper and the lower edges of the fins and the like, the following judgment is performed.

The fin width (FinWid) can be found from the edge positions of the upper and the lower edges of the fins, so judgment of fin detects can be made using the minimum value (FinWidMin) and maximum value-(FinWidMax).

The fin pitch total obtained from the image information is obtained from the position information of the edges. If this is compared with the fin pitch total obtained from the product number information, defects can be detected.

If the difference between the Y-coordinate of the "n"th edge and the Y-coordinate of the "n+1"th edge is taken, ½ the value of the fin pitch is obtained. The fin pitch intervals are statistically processed to determine the average (FinGapMean), standard deviation (FinGapStd), minimum value (FinGapMin), and maximum value (FinGapMax) for judgment. Below, this statistical processing is called the "statistical processing of the pitch intervals" of the fins. If the minimum value (FinGapMin), maximum value (FinGapMax), and average (FinGapMean) are within empirically obtained predetermined values, they are deemed good parts. For standard deviation (FinGapStd), if the fin pitch is abnormal, it can be judged that it is off from the predetermined value.

Next, frequency analysis of fins will be explained. The object is to increase the inspection accuracy of defect modes relating to fin pitch defects by combining the above judgment with inspection. The method of creating a base waveform will be explained referring to the images B of FIG. 7.

In a third window, if projecting brightness in the X-axis direction for an already obtained fin image (adding brightness in the horizontal direction, that is, the cumulative sum), as shown in an image B, a sine wave like waveform is obtained. In a normal case, a clear sine wave is exhibited, however, when there is a defect, the waveform loses its shape. Therefore, by examining the frequency components of these waveforms, judgment of defects becomes possible. In each image B of FIG. 7, in a waveform (which is called "cumulative sum waveform of the fins") shown by discrete lines in the Y-axis direction, the Y-axis direction represents the position and the X-axis direction represents the cumulative sum of the brightness.

The inspection method of investigating these frequency components may be performed by the wavelet analysis technique. When wavelet analysis is performed, the vertical axis will show the frequency by wavelet analysis of the cumulative sum waveform of the fins, the horizontal axis will show the positions of the fins. The frequency range in which the frequency of the cumulative sum waveforms of normal fins exists can be predetermined. A total sum of the values of the frequency components added together in the predetermined frequency range across the positions of the fins, can be obtained. Defects (irregular pitch etc.) may be judged by deeming the fins as good parts if the total sum of the values of the frequency components is over a predetermined value, and as defects if no more than that. Further, if analyzing the variations of the frequency, because the normal pitch is erratic in the case of buckling, buckling defects can be identified.

Figure 8:
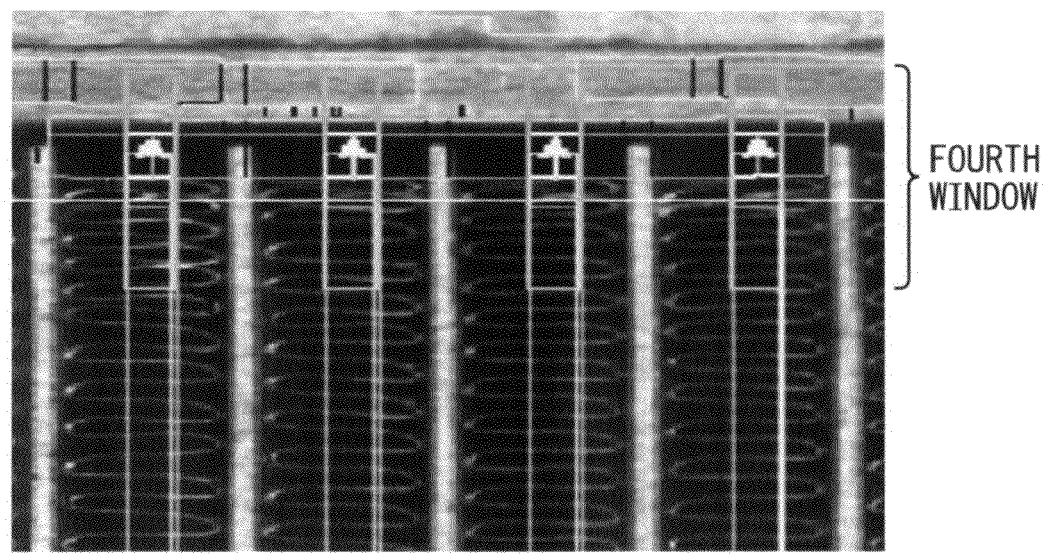
FIG. 8 is an explanatory view of processing for detecting short fins.

The processing for detecting short fins will be explained. A short fin, as has already been explained, is a defect in which the distances between the two fin ends and the sheet metal 16 are abnormal. In order to detect this defect, when the fourth windows are set, images at the fin ends are extracted at the common areas of the fourth windows and the third windows. Here, because the positions of the sheet metal 16 are already known, the edge of a first fin from a sheet metal end is treated as the furthermost edge of the fins and the distance between the sheet metal end and the first fin (FinUPGap and FinBottomGap) is found and compared to a predetermined value to judge for defects (judge for rows other than the outermost rows). At the set window, judgment may be made by looking at whether the minimum value and maximum value are within a predetermined range. FIG. 8 is an explanatory view of processing for detecting short fins. Note that judgment of short fin defects is not performed for the two ends (outermost rows) of the fourth windows.

Among the fin defects, irregular pitch, erosion, crushing, and buckling can generally be judged by statistical processing of the pitch intervals.

Figure 2:
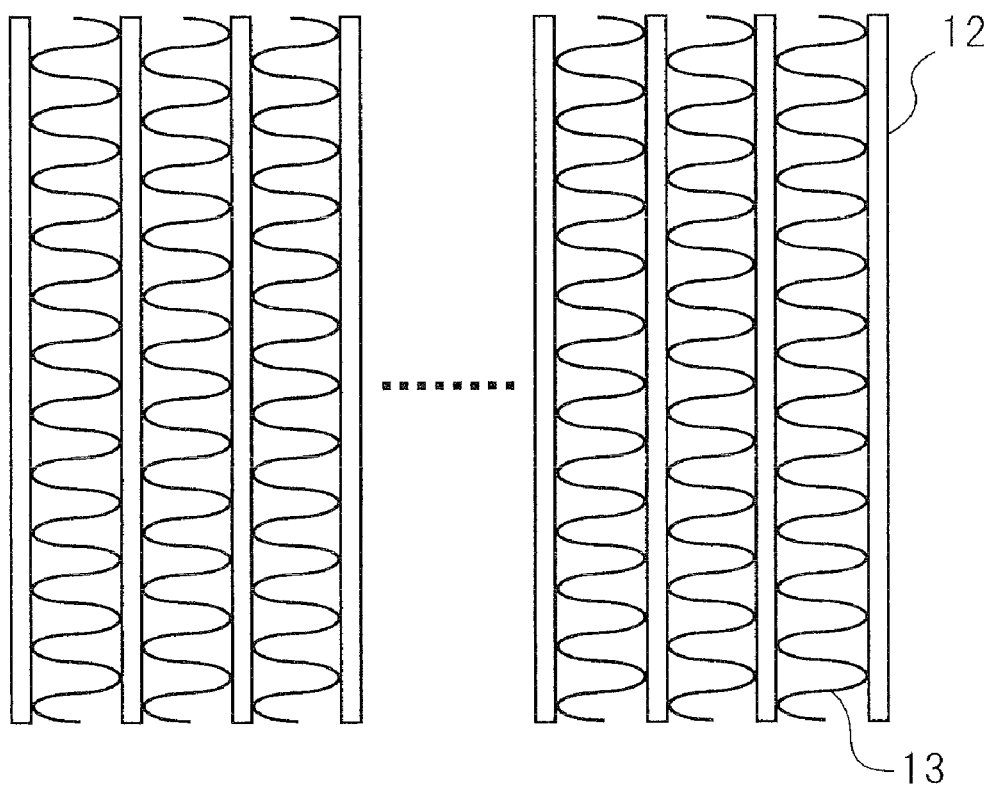
FIG. 2 is a view rotating the heat exchanger 10 of FIG. 1 by 90 degrees and showing the fin and tube part enlarged.
Figure 3:
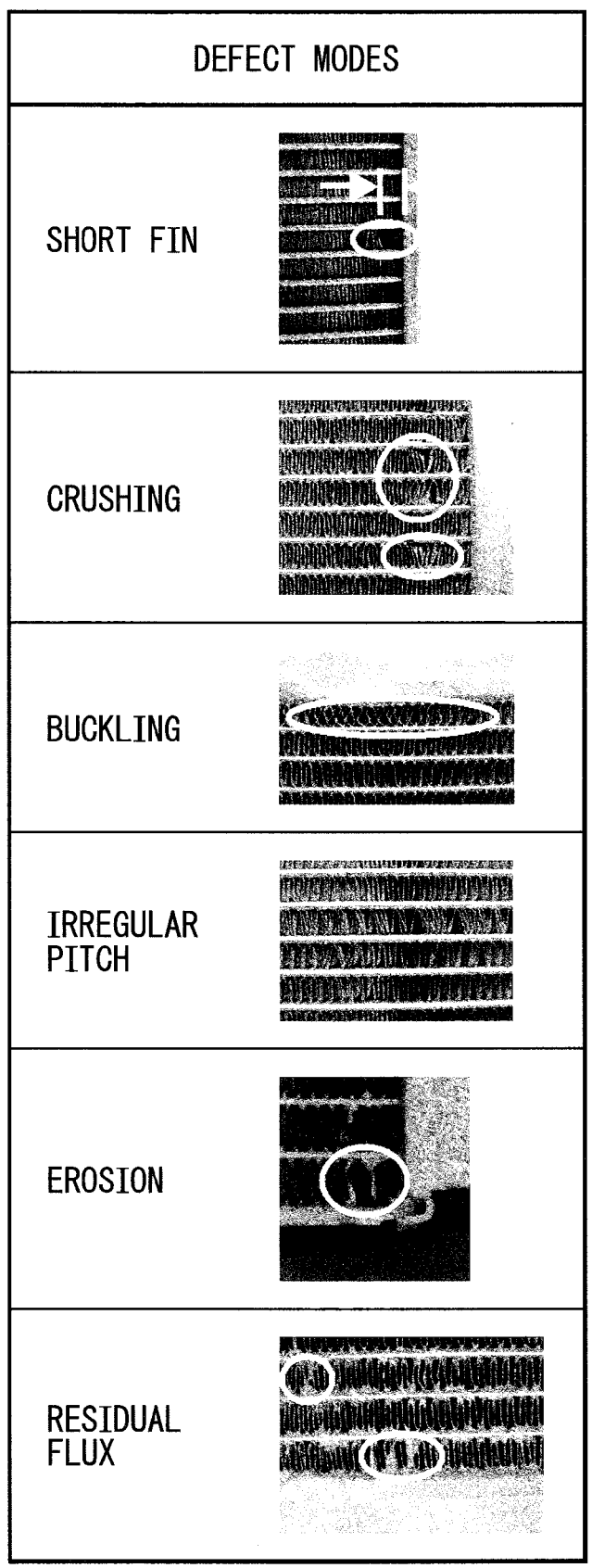
FIG. 3 is a view showing examples of fin defects.

For crushing, since the upper and lower ends of the fins (the upper and lower ends in the vertical direction when the core surface shown in FIG. 2 is placed horizontally) are bent, they will reflect light and become bright (white) lumps. Thus, in order to find these, the thin parts of normal fins are erased (normal fins are erased by opening processing) and the remainder judged to be fin crushing defects.

For buckling defects, because the tube positions are already known by the analysis at the second window, the distances between the tubes are calculated in a range of several tubes (three for example) from a side plate 15 and compared with a normal value (the "normal value" being the average value of tube pitches within the second window or the value obtained from the product dimension data or the like plus or minus a predetermined value to obtain the normal range). If all are not abnormal, it may be judged that there is no buckling. That is, if an abnormal value appears in the tube pitches at a second window in the vicinity of a side plate 15 (not necessarily three tubes), it is judged that there is buckling.

If using the tube image at a later mentioned fifth window to calculate the tube pitches for the entire length of a tube in the long direction in the vicinity of a side plate 15, abnormalities in tube pitches may be detected with better accuracy.

For residual flux defects, these defects may be judged by comparing the fin pitch total with the fin pitch total obtained from the product information. As an alternative method, a residual flux defect may also be judged to exist when a maximum value of fin width (FinWidMax) obtained from the edge positions of the upper and the lower edges of the fins is greater than a predetermined value.

Residual flux defects may also be found from tube width abnormalities. In this case, in the first window, a fifth window is set for each unit tube. This window is divided into small regions and averaging is performed for each small region. By taking the difference between the brightness of the averaged image and the raw image and extracting the image having a predetermined brightness from the raw image, the remaining image is left with only the tubes. To remove the noise, opening processing is performed. Afterwards, in the fifth window, the tube is surrounded by a rectangle, the sides of the rectangle are shortened until any point of the tube contacts the rectangle, the sides of the rectangle at that time are found (called smallest rectangle surrounding tube), and the X-axis direction width t is calculated. If the width t is greater than a predetermined value deemed to be a residual flux defect, it may be judged to be a residual flux defect.

Figure 9:
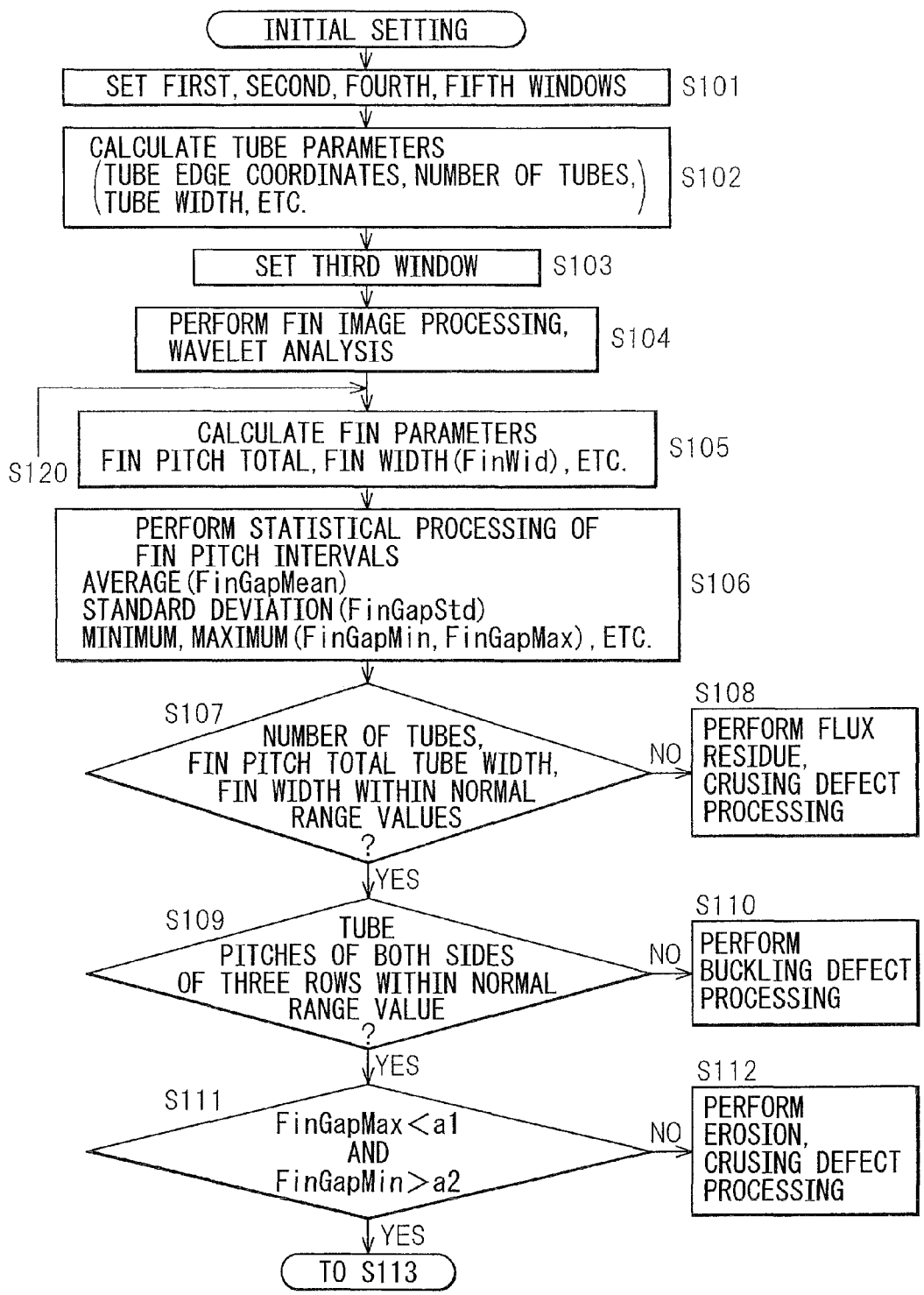
FIG. 9 is a schematic flowchart of a first embodiment of the present invention.
Figure 10:
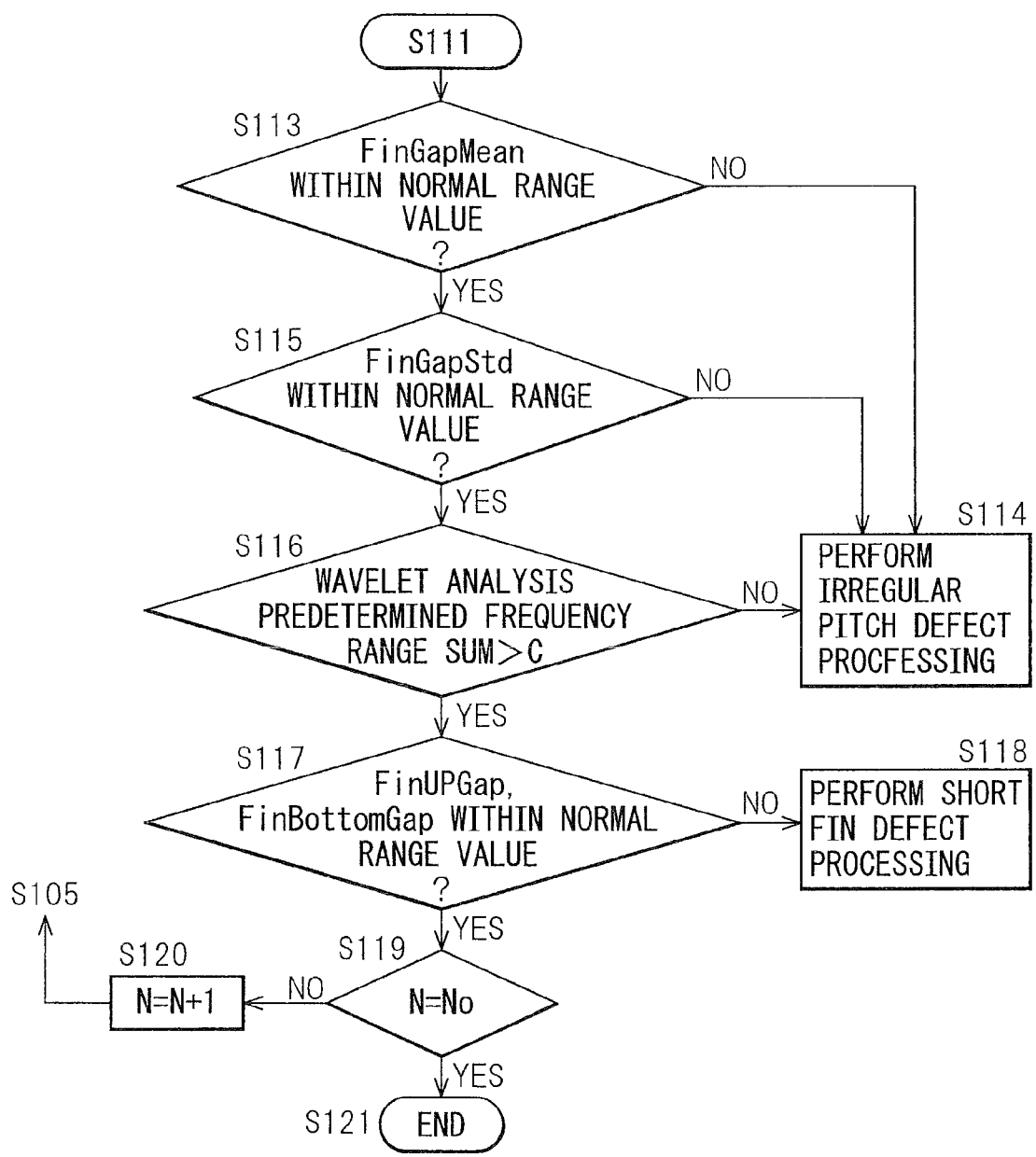
FIG. 10 is a schematic flowchart of a first embodiment of the present invention.

FIGS. 9 and 10 are schematic flowcharts regarding the first embodiment of the present invention. The above fin defects will be explained following the flowcharts of FIG. 9 and 10.

At step S101, the first, second, fourth, and fifth windows are set. At step S102, the tube edge coordinates from the edges of the two sides of each tube in the second window, the number of tubes, and tube width may be calculated. Further, in the fifth window, the maximum value of the tube width across the Y-axis direction of each tube is obtained. At step S103, because the tube edge coordinates of the two sides of each tube are already known, the third window may be set.

At step S104, the image of the fins in the third window is image processed, the fins are extracted, and wavelet analysis is performed on the fin waveforms. The processing from steps S102 to S104 is performed for all the tubes and fins in the first window. At steps S105 and S106, the parameters for the fins are calculated and statistical processing is performed for the pitch intervals of the fins.

At step S107, the number of tubes, fin pitch total, tube width (tube width obtained by processing at the fifth window), and fin width are compared with the information obtained from the product number information to judge if the values are within the normal range. If NO, at step S107, the routine proceeds to processing for residual flux and crushing defects. If YES, at step S109, the routine proceeds to judgment for buckling defects. If tube pitches of both sides of three rows are within normal range value, the routine proceeds to step S111, and if not, to step S110.

At step S111, if the maximum value obtained from statistical processing of the pitch intervals (FinGapMax) is compared with a predetermined value a1 for obtaining a normal range obtained empirically and found to be smaller, and if the minimum value (FinGapMin) is compared with a predetermined value a2 for obtaining a normal range obtained empirically and found to be larger, the routine proceeds to step S113. If not, the routine proceeds to the processing for erosion and crushing defects at step S112.

At steps S113 and S115, it is judged if the average (FinGapMean) and the standard deviation (FinGapStd) are within normal ranges empirically obtained. If so, the routine proceeds to step S116. If not, the routine proceeds to the processing for irregular pitch defects at step S114.

At step S116, the wavelet analysis method is used to judge for defects. If the total sum of the values of the frequency components added together in the predetermined frequency range across the positions of the fins is a predetermined value c or more, the part is judged to be a good part. If NO, the routine proceeds to the processing for irregular pitch defects at step S114. The processing at step S116 may also be omitted and the routine made to proceed to step S117.

At step S117, the routine proceeds to judgment of short fin defects. If FinUPGap and FinBottomGap are not within normal range value, the routine proceeds to step S118, and if YES, to step S119. The processing ends at step S121. The processing from step S105 to step S119 may be performed for each row of fins between adjacent tubes and may be performed for each of a predetermined number of rows of fins or for all fins.

The defect processing at steps S108, S110, S112, S114, and S118 may be determined according to the characteristics of each. The same defect processing may be performed in all cases. According to the accuracy of defect judgment at each step, a portion may be automatically handled as a defect while the remainder may be visually inspected and manually selected and corrected.

Figure 11:
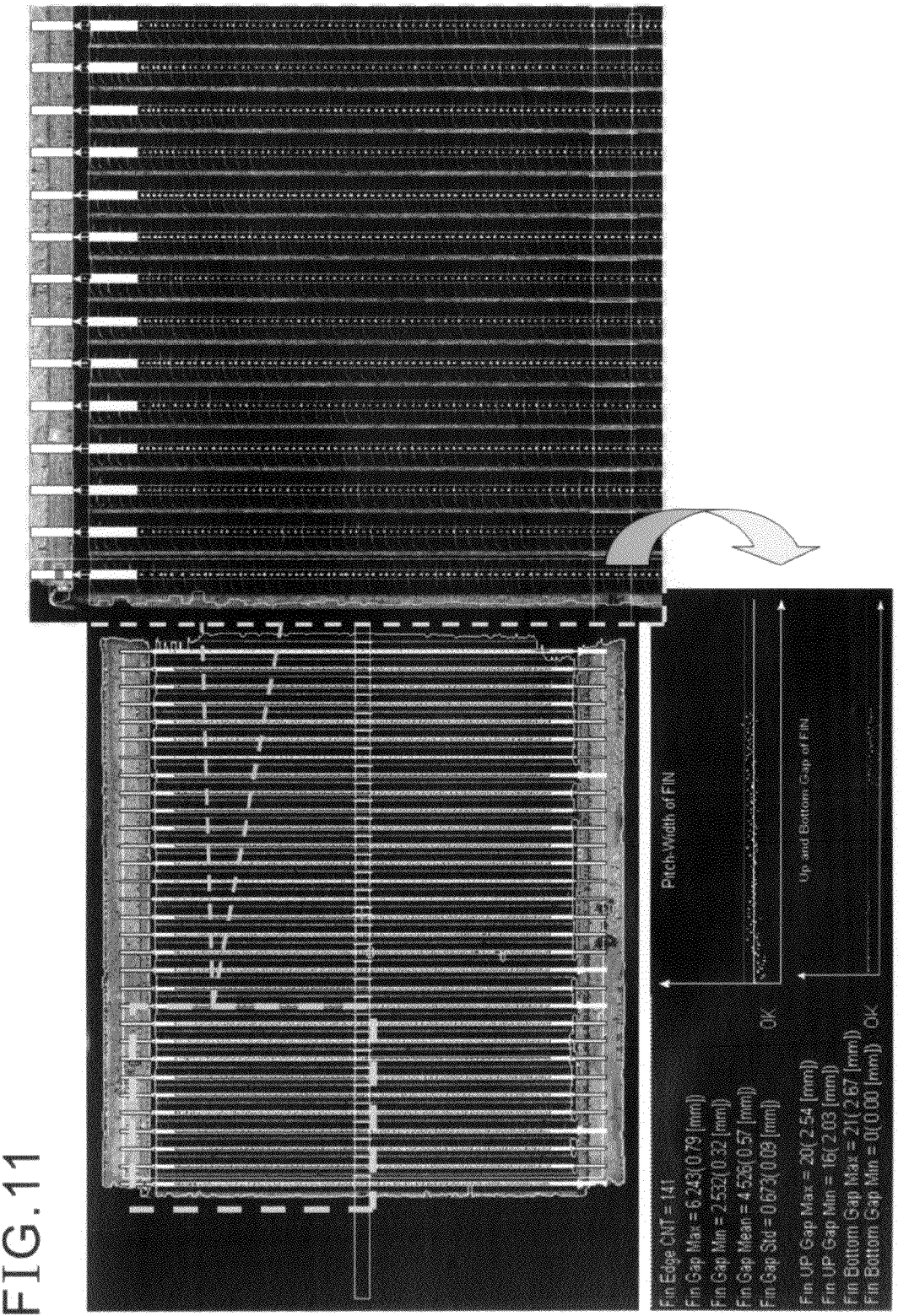
FIG. 11 is an explanatory view of an embodiment using the fin inspection method for only one part of the fins.

As a second embodiment, the judgment of fin defects may be limited to part of the air flow area of the fins particularly impacting the capability of a heat exchanger. The inspection method may also be performed only for any other part as well. FIG. 11 is an explanatory view of an embodiment applying the fin inspection method to only one portion of the fins.

Figure 12:
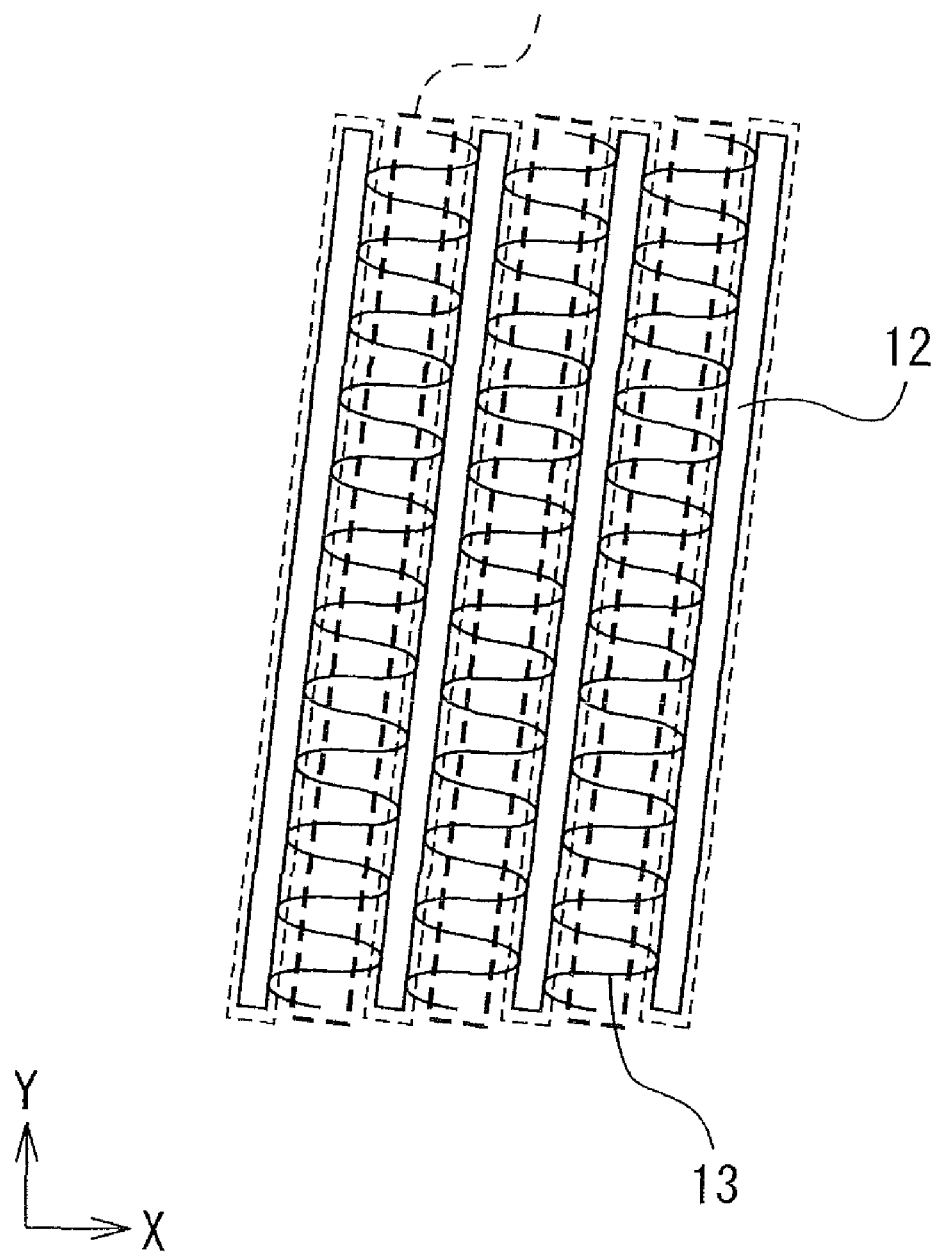
FIG. 12 is an explanatory view of a third embodiment for a parallelogram-shape core.

As a third embodiment, the method of setting the third windows for a parallelogram-shape core is explained below. FIG. 12 is an explanatory view of the third embodiment. The third windows are corrected so as to be inclined along the long direction of the tubes, according an average of angles of inclination of the tubes for X-axis. When the images of the tubes are extracted in the method stated in paragraph [0045], an average of angles of inclination of the tubes can be calculated from center coordinates between the edges of the two sides of the tubes, along the long direction of the tubes. The angle of inclination of each tube can be also calculated by rotating the smallest rectangle surrounding tube in the fifth window.

Figure 13A:
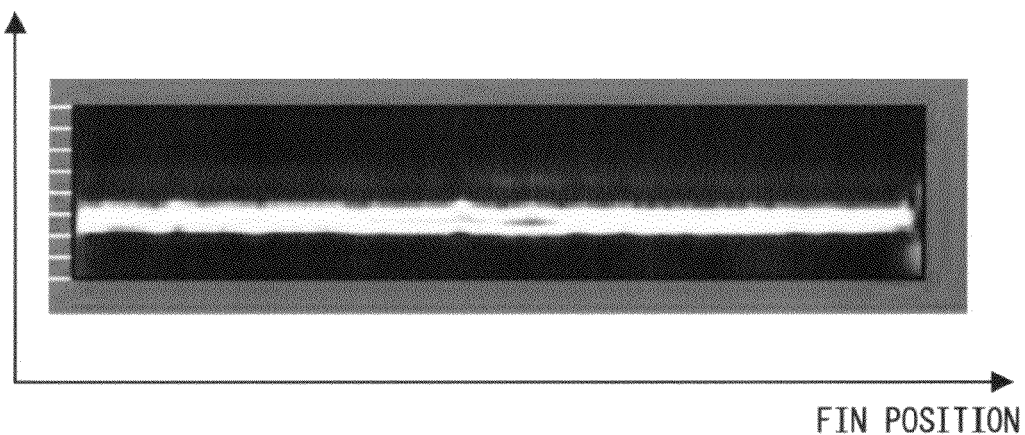
FIG. 13A is a view of a wavelet analysis image of normal fins.
Figure 13B:
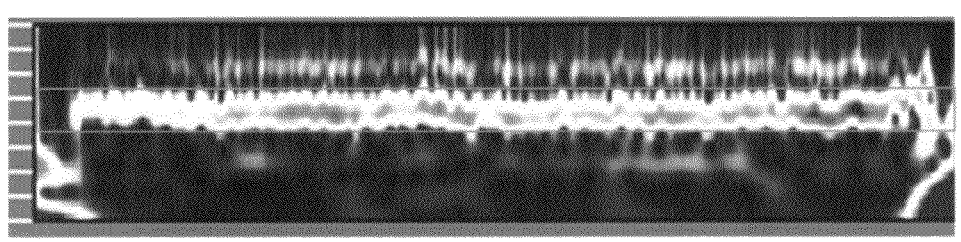
FIG. 13B is a view of a wavelet analysis image of fins to be inspected.

The wavelet analysis technique as explained in paragraph [0058] is further explained below. FIG. 13A is a view of a wavelet analysis image of normal fins. FIG. 13B is a view of a wavelet analysis image of fins to be inspected. The frequency range in which the frequency of the cumulative sum waveforms of normal fins exists can be predetermined. As a fourth embodiment, the wavelet analysis images can be colored in red and blue, wherein red areas indicate high intensity of the frequency components and blue areas indicate low intensity of the frequency components in the predetermined frequency range (if FIG. 13B is colored). In black and white images, white areas indicate high intensity of the frequency components and black areas indicate low intensity of the frequency components. Defects may be judged by deeming the fins as good parts if the area size of the total white area of the frequency components is over a predetermined value, or the total sum (a kind of volume) of the values of the frequency components in the predetermined frequency range is over a predetermined value.

While the present invention was explained in the case of an automobile heater, it may be used for the inspection of normal radiators as well.

As explained above, according to the present invention, inspections with higher accuracy may be performed in fin inspections.

The invention claimed is:

1. An inspection method of a core of a heat exchanger provided with fins and tubes comprising
   a step of having an imaging device capture an image of the core and inputting into an image processing device the image data for storage,
   a step of setting a first region in the image data in which an image of the entire core is captured and setting a second region in which an image of at least a portion of all of the tubes is captured so as to identify position information of the tubes,
   a step of setting a third region for fin detection between adjacent tubes based on the identified position information of the tubes,
   a step of performing binarization changing thresholds and noise removal in the third region to obtain an image of the fins and identifying from the image of the fins the edge position information of the fins along a long direction of the tubes, and
   a step of performing statistical processing of the pitch intervals based on the edge position information of the fins and judging fin defects.

2. An inspection method of a core of a heat exchanger as set forth in claim 1 further comprising
   a step of performing processing on the image of the fins at the third region, for adding brightness of the image in a direction perpendicular to the long direction of the tube, across the long direction of the tube to obtain a waveform across the long direction of the tube and
   a step of analyzing the waveform by wavelet analysis to find a total sum of frequency components added together in a predetermined frequency range across the long direction of the tube to judge fin defects.

3. An inspection method of a core of a heat exchanger as set forth in claim 1 further comprising
   a step of setting a fourth region for short fin defect detection encompassing the upper end or lower end of all of the tubes and
   a step of calculating the distance between a tank part of a core of the heat exchanger and the fin edge position in the greatest proximity with it in a common region of the third region and the fourth region to judge fin defects.

4. An inspection method of a core of a heat exchanger as set forth in claim 1 further comprising a step of extracting an entire single tube from the image data, then finding the smallest rectangle surrounding the tube and calculating the width of the tube to judge fin defects.

5. An inspection method of a core of a heat exchanger as set forth in claim 1, wherein the third region for fin detection between adjacent tubes is corrected according to an average of angles of inclination of the tubes.

* * * * *